US005474546A

United States Patent [19]
Ambrisco et al.

[11] Patent Number: 5,474,546
[45] Date of Patent: Dec. 12, 1995

[54] DRIPLESS CANNULA SYSTEM USABLE WITH A SAMPLING CONTAINER FOR FLUID SAMPLING AND OPERABLE TO MINIMIZE FLUID LOSS AT A FLUID SAMPLING SITE

[75] Inventors: William M. Ambrisco, Hayward; Lauretta A. Iwamasa, Newark; Jack E. Ulstad, Boulder Creek, all of Calif.

[73] Assignee: Abbott Laboratories, Abbott Park, Ill.

[21] Appl. No.: 239,499

[22] Filed: May 9, 1994

[51] Int. Cl.⁶ ............................... A61M 5/24; A61M 5/28; A61M 5/00; A61M 5/32
[52] U.S. Cl. ........................... 604/411; 604/244; 604/201
[58] Field of Search ................................ 604/51–53, 93, 604/192, 198, 201, 213, 244, 411, 414; 128/764, 765

[56] References Cited

U.S. PATENT DOCUMENTS

| | | | |
|---|---|---|---|
| D. 320,082 | 9/1989 | Wyatt et al. | D24/129 |
| 323,709 | 2/1992 | Wyatt et al. | D24/129 |
| 4,219,912 | 9/1980 | Adams | 128/214 |
| 4,412,573 | 11/1983 | Zdeb | 604/415 |
| 4,610,469 | 9/1986 | Wolff-Mooij | 604/411 |
| 4,763,648 | 8/1988 | Wyatt | 128/673 |
| 5,002,066 | 3/1991 | Simpson | 128/760 |
| 5,048,537 | 9/1991 | Messinger | 128/673 |
| 5,086,783 | 2/1992 | Macors et al. | 604/244 |
| 5,122,117 | 6/1992 | Haber et al. | 604/201 |
| 5,135,489 | 8/1992 | Jepson et al. | 604/48 |
| 5,147,329 | 9/1992 | Brannon | 128/764 |
| 5,148,811 | 9/1992 | Messinger | 128/673 |
| 5,158,554 | 10/1992 | Jepson et al. | 604/411 |
| 5,201,717 | 4/1993 | Wyatt et al. | 604/192 |
| 5,203,775 | 4/1993 | Frank et al. | 604/256 |
| 5,242,393 | 9/1993 | Brimhall et al. | 604/86 |
| 5,242,423 | 9/1993 | Goodsir et al. | 604/243 |
| 5,309,924 | 5/1994 | Peabody et al. | 128/765 |
| 5,324,256 | 6/1994 | Lynn et al. | 604/201 |
| 5,380,281 | 1/1995 | Tomellini et al. | 604/411 |

OTHER PUBLICATIONS

U.S. patent application Ser. No. 89/00273 filed Jan. 23, 1989 by Jepson et al.
U.S. patent application Ser. No. 90/01350 filed Mar. 16, 1990 by Jepson et al.

*Primary Examiner*—C. Fred Rosenbaum
*Assistant Examiner*—Frank Wilkens, III
*Attorney, Agent, or Firm*—Harry G. Thibault; Thomas M. Breininger

[57] ABSTRACT

A dripless cannula system usable with a syringe or other fluid container in a fluid sampling procedure and operable to minimize retention of residual fluids at a sampling site following the sampling procedure. In the preferred embodiment, a vacuum chamber operatively connected to a blunt cannula of the dripless cannula system is operative upon withdrawal of the cannula from the sampling site to draw residual fluids at the site into the vacuum chamber for subsequent disposal. The dripless cannula system of the present invention is a simple, effective apparatus for minimizing the presence of residual fluids at a sampling site following a sampling procedure.

32 Claims, 8 Drawing Sheets

DRIPLESS CANNULA SYSTEM USABLE WITH A SAMPLING CONTAINER FOR FLUID SAMPLING AND OPERABLE TO MINIMIZE FLUID LOSS AT A FLUID SAMPLING SITE

BACKGROUND OF THE INVENTION

1. Field of the Invention

The present invention relates generally to fluid sampling apparatus and in particular to a dripless cannula system usable in connection with a fluid sampling site to minimize user contact with trace fluid occurring at the port during the fluid sampling procedure.

2. Discussion of the Prior Art

In a hospital setting there is always the need to monitor patient health through the evaluation of a blood chemistry profile. The simplest method employed in the hospital is to use a syringe carrying a sharpened cannula at one end and insert that cannula into a vein or artery to extract a blood sample from the patient. However, such a procedure exposes the patient to airborne bacteria and viruses which can enter through the opening made by the needle during the blood sampling process and the nurse or technician may be exposed to blood borne pathogens if they accidentally jab themselves with a used needle carrying such pathogens.

Moreover, it is an anomaly that the more seriously ill the patient is, generally the more often such blood sampling procedures must take place to monitor the blood profile and examine the level of pathogens in the blood. Accordingly, when an alternative to direct sampling from a vein or artery is available to the nurse or clinician monitoring the health of the patient that alternative is actively pursued. Thus the increased utilization of indwelling arterial or venous catheters in critically ill patients has lead clinicians to, whenever possible, use such arterial or venous lines for blood sampling.

To expedite sampling in such arterial or venous lines, stopcocks and injection sites or sampling ports have been provided in such lines to facilitate blood sampling. Stopcocks were added to facilitate blood sampling before sampling ports were used. However, stopcocks increased contamination and risk of infection and increased blood waste. Sampling sites eliminated many of the concerns associated with both directly drawing and using stopcocks to withdraw a blood sample from the patient. The catheter associated with such line was securely placed in the patient and needed to be placed only once to minimize pain, puncture wounds, the chance of damaging surrounding tissue and organs, and the possibility of infection to the patient caused by multiple samplings.

Thus in the earliest design of remote sampling sites to be placed in arterial or venous lines the focus was on infection to the patient and such lines were typically designed for use with sharp cannulae. Typically such sites were formed of a housing having a fluid flow path therethrough, with access to the fluid flow path provided through a membrane or septum disposed in the housing so as not to interfere with or impede such fluid flow path. An example of such a sampling port is shown in U.S. Pat. No. 4,673,648 entitled "METHOD AND APPARATUS FOR ARTERIAL AND VENOUS BLOOD SAMPLING" and issued Aug. 16, 1988.

The earliest uses of such sampling sites were with sharpened cannulae. The sharpened cannulae were forced through the septum to be placed into fluid flow communication with the fluid path through the housing. Repetitive piercing of the septum in such injection sites were a source of physical damage to the septum. Such damage, known as coring or laceration, could shorten the effective life of the injection site.

Moreover such an apparatus failed to eliminate the possibility of the nurse or clinician using a sharp cannula from being infected by blood borne pathogens caused by an accidental stick with the sharpened cannula following extraction of a blood sample from a patient.

Consequently, the next step in the evolutionary development of the dripless cannula was the development of a blunt cannula to be used with a sampling site. In such configuration the sampling site was also provided with a slit to facilitate insertion of the blunt cannula into the sampling site for extraction of a blood sample from the patient. The blunt cannula solved one part of the problem associated with a blood draw from a sampling site in that such blunt cannula would not pierce the skin of the user.

However, the possibility of infection by a blood borne pathogen to the user remains since the blood at the sampling site and in the syringe was typically under arterial or venous pressure seen at the sampling site or the distal tip of the cannula, and in extreme cases could cause a fine spray of blood to contact the user and thus still cause contact between the clinician or nurse treating the patient and the blood borne pathogens of the patient.

Accordingly, it would be desirable to so modify the sampling site and/or the cannula system associated with such sampling site for performing a fluid draw procedure at the site so as to minimize the possibility of blood droplets remaining at the sampling site following a sampling procedure while retaining all of the advantages inherent in a blunt cannula system usable with a resealable slit as such system has evolved from the earliest stages of blood sampling procedures.

Further it would be desirable if such improved sampling system comprise a simple adjunct to the blunt cannula requiring few additional parts, be integrally joined with the blunt cannula for simplicity of operation, and further enable simplicity of operation to minimize operator error in the blood draw process which would unnecessarily expose the clinician to blood borne pathogens.

SUMMARY OF THE INVENTION

The present invention incorporates into a blunt cannula a method and apparatus for removing trace or residual blood associated with blood sampling at a sampling site to minimize the possibility of user contact with the blood of the patient. In one embodiment of the present invention, a vacuum chamber is disposed above the distal end of the cannula to receive trace amounts of blood remaining at the sampling site when the cannula is removed from the sampling site following the sampling procedure.

The preferred embodiment envisions two alternative configurations. In a first configuration, an outer cannula encloses an inner cannula and the vacuum chamber is disposed above the inner cannula with the inner cannula passing through the vacuum chamber for reciprocal movement therein. A sealing disc associated with the inner cannula is disposed in and seals the cylindrical vacuum chamber. Following a blood draw, the dripless cannula device is removed from the sampling site by drawing up the inner cannula to provide a vacuum in the vacuum chamber to draw blood through the interstitial space between the inner cannula and the outer cannula into the vacuum chamber to remove any residual blood remaining at the sampling site immediately following the blood sampling procedure.

In an alternative configuration, a metal cannula interfaces with a vacuum chamber. When the cannula is installed onto the sampling container, the annular sealing member associated with the vacuum chamber and mounted on the cannula is pushed to the upper end of the chamber. As the cannula is withdrawn from the septum of the sampling site, an annular retaining ring at the lower end of the cannula engages the septum to draw the sealing ring down and allow residual blood associated with the sampling process to be drawn into the vacuum chamber.

In a second alternative embodiment of the present invention, instead of disposing a vacuum chamber around the cannula to receive residual blood associated with the sampling process, a plug of resilient absorbent material is disposed about the cannula, such material compressed against an upper wall of an associated shield when the cannula is inserted into the sampling port, such material to expand when the cannula is removed from the sampling port, with the absorbent qualities of the plug to allow it to soak up any residual blood at the sampling site following the sampling procedure.

The present invention offers a simple, effective system for removing residual blood from a sampling site. Such system requires a minimal number of parts, is integrally associated with the cannula to improve efficiency, and solves a problem previously not addressed in the industry. The dripless cannula system of the present invention is usable with a syringe or other fluid container used for fluid sampling and such system is operable to minimize fluid contact with the hospital clinician at a fluid sampling site.

Such system comprises a blunt cannula having a distal end receivable in the septum of a fluid sampling site and a proximal end connectable to a fluid container in locking fluid-tight engagement therewith to provide a fluid path from said sampling site to said syringe. Fluid removing apparatus is disposed about the cannula between the sampling site and the syringe, such apparatus operable following withdrawal of the cannula from the sampling site to receive residual fluids disposed at the sampling site by the sampling process.

A better understanding of the present invention can be obtained by a consideration of the detailed description set forth below, such detailed description to be considered with the drawings provided. Such drawings are briefly described below.

DETAILED DESCRIPTION OF THE INVENTION

Figure 1:
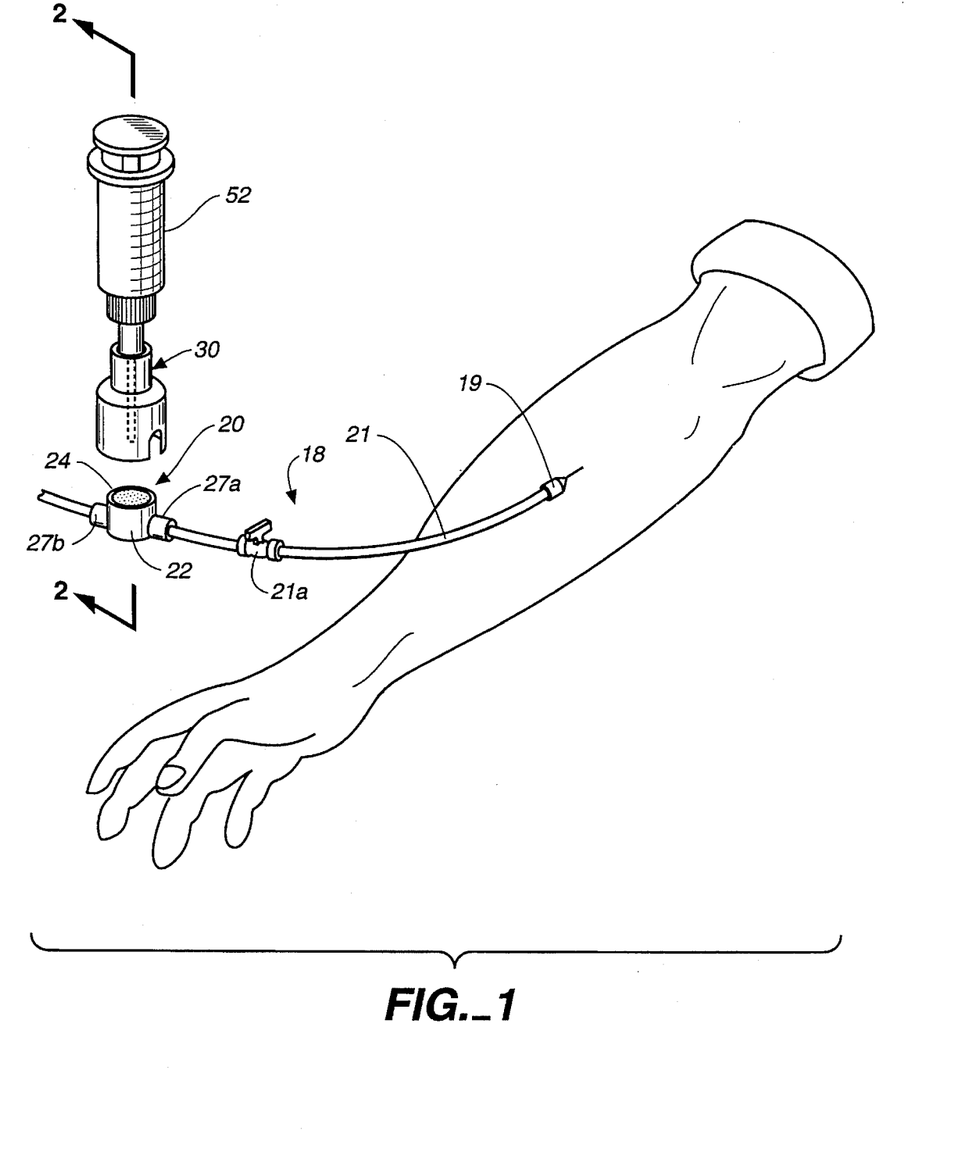
FIG. 1 is schematic view of a portion of a pressure monitoring apparatus connected to a patient, with the dripless cannula system of the present invention connected to a fluid container and disposed above a sampling site of such monitoring apparatus.

The dripless cannula system 30 of the present invention is typically used with a blood pressure monitoring system 18 schematically shown in FIG. 1. A catheter 19 inserted into a patient, is connected to a fluid input line 21. Disposed in line 21 is a sampling site 20 having a housing 22 and input and output lines 27a, 27b and a stopcock 21a. The dripless cannula system 30 is provided on a syringe 52 for engagement with sampling site 20 to perform a blood draw.

The preferred embodiment of the present invention is shown in FIGS. 2–7, in which the sampling site or sampling port 20 comprises a body 22 having a septum or bung 24 of relatively soft or flexible material such as silicon disposed at one side to provide access to a fluid flow through path 26 in the site which is connected to input and output lines 27a, 27b.

Figure 2:
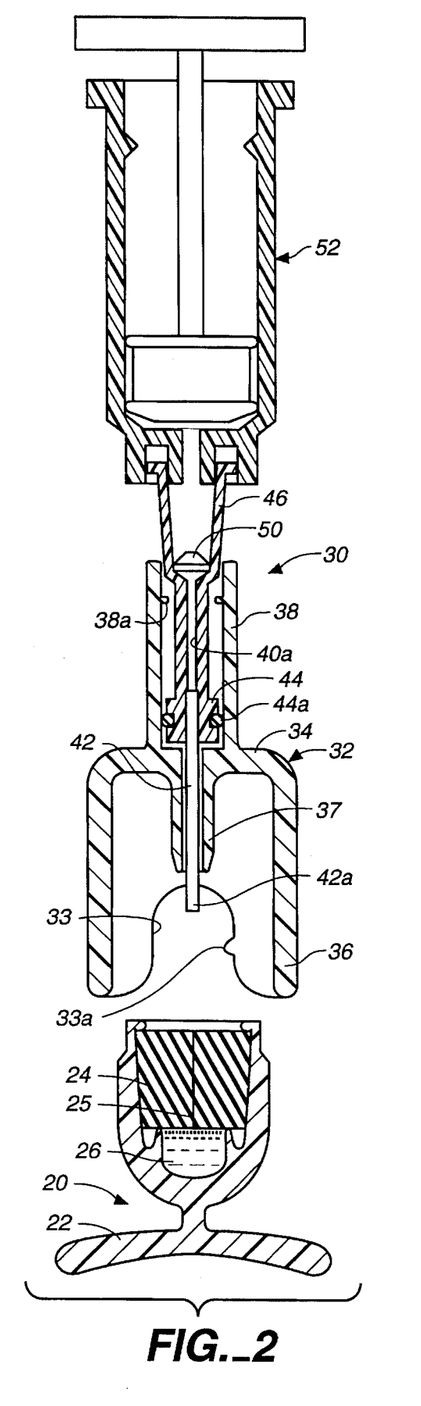
FIG. 2 is a sectional view taken generally along lines 2—2 of FIG. 1.

Referring to FIG. 2, the dripless cannula system 30 of the present invention comprises a cylindrical outer shield 32 in which a cylinder 36 extends downwardly from a base 34. In this cylinder 36 is about 1.3 cm in diameter and 1.6 cm long, although size is not a critical factor and other lengths and diameters are possible. Slots 33 are provided on opposite sides of shield 32, at a lower end thereof. Detents 33a project into slots 33 at the lower end thereof. Also extending downwardly from the base 34 is a centrally mounted blunt outer cannula 37. Extending upwardly from the base 34 is a cylindrical vacuum chamber 38, which is about half the diameter of the cylindrical outer shield 32, or about 0.60 cm in the embodiment shown. The chamber 38 also can vary in length but is about 1.30 cm long in the preferred embodiment of FIGS. 2–7. An end stop 38a is provided at the upper end of vacuum chamber 38.

A fitment 40, disposed in the vacuum chamber 38 connects an inner cannula 42 to a syringe 52. The fitment 40 is about 2.0 cm long in the embodiment of FIGS. 2–7 and at a lower end carries an annular shoulder 44, which carries thereon an O-ring 44a which provides a seal for vacuum chamber 38, the O-ring seal 44a shown near the bottom of vacuum chamber 38 in FIG. 2. The metallic inner cannula 42 is fixedly mounted at a proximal end thereof to the modified fitment 40 which fixedly engages inner cannula 42 at a lower end to connect the inner cannula to a flowthrough bore 40a of the fitment thereof slightly above the annular shoulder 44. The upper end of fitment 40 includes luer lock section 46 connectable to the syringe 52.

Disposed within the cannula luer lock section 46 is a duckbill one-way valve 50 which allows fluid flow in one direction only, through the inner cannula 42, the channel 40a of fitment 40 and into the syringe 52. Although it may not be necessary to include a one-way valve to provide an operative dripless cannula system, the valve is shown in the preferred embodiment. The metallic inner cannula 42 is reciprocably moveable within the vacuum chamber 38.

In operation, the luer lock section 46 of fitment 40 is connected at a locking upper end 48 to the syringe 52. The fitment 40 is lowered to the bottom of the vacuum chamber 38 to slide inner cannula 42 through outer cannula 37 to extend a distal end or tip 42a of the inner cannula about 0.60 centimeters below the inner end or tip 37a of the outer cannula 37 and dispose the sealing ring 44a at a lower end of the vacuum chamber 38.

Figure 3:
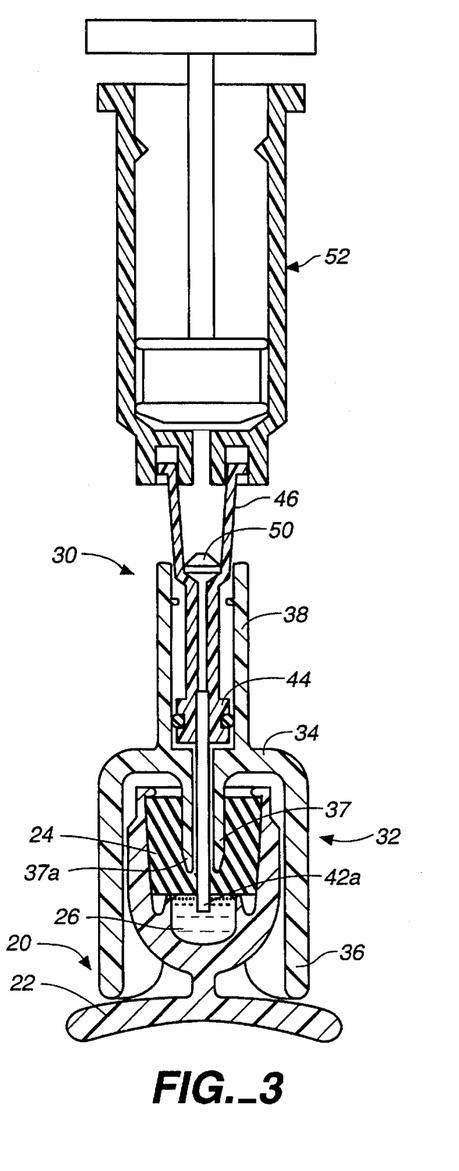
FIG. 3 is a view similar to FIG. 2 wherein the dripless cannula system of the present invention has been introduced into the sampling site to place the cannula in the fluid flow path of the sampling site for a blood draw.
Figure 4:
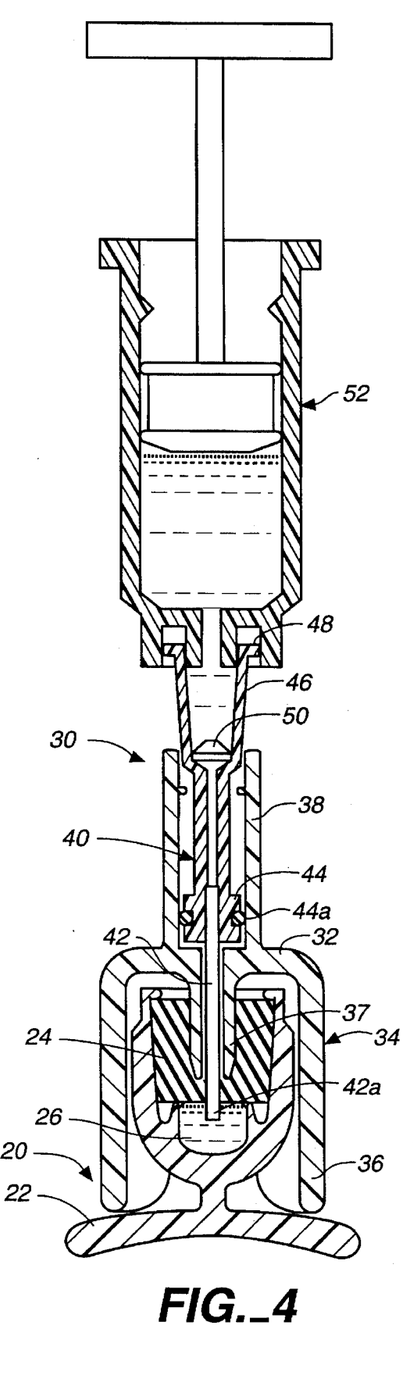
FIG. 4 is a view similar to FIG. 3 in which a blood draw is in progress at the sampling site.

Then, as shown in FIG. 3, the dripless cannula system 30 of the present invention is inserted into the slit reseal sampling site 20, with the inner cannula 42 first entering the resealable slit 25 in the septum 24 and followed therein by the outer cannula 37 to place the inner cannula in the fluid path 26 of the sampling site 20 to enable a blood draw from the sampling site 20.

In the installed position of FIG. 3 outer shield 32 overlies the site 20 to place input, output lines 27a, 27b in slots 33, with detents 33a underlying lines 27a, 27b to hold cannula system 30 in place on the sampling site 20. The outer cannula 37 is disposed within the septum 25 and displaced from the fluid path 26, with the distal end of the inner cannula 42 in the fluid path 26.

Figure 5:
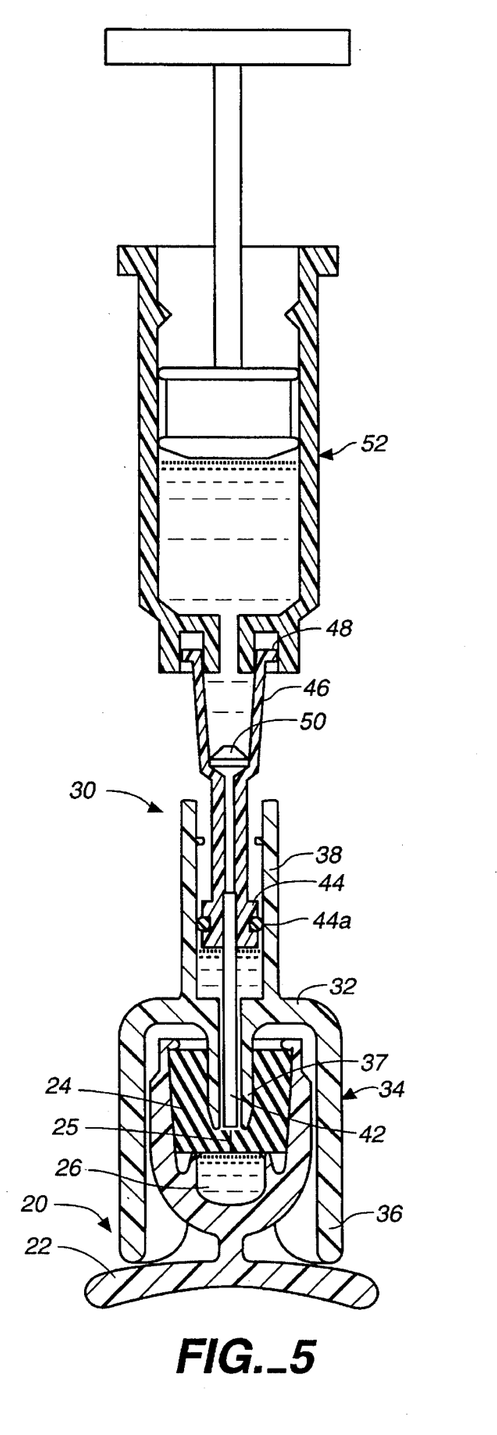
FIG. 5 is a view similar to FIG. 4 wherein the blood draw is complete, the cannula has been removed from the flow path through the sampling site and the dripless cannula system of the present invention has not yet been removed from a septum associated with the sampling site.

At the sampling site 20, arterial or venous blood is under pressure, typically 120 to 300 ml of mercury above atmospheric pressure. With the inner cannula 42 in fluid flow path 26, a flood draw is commenced, such blood draw shown in progress in FIG. 4. Once the blood draw is completed, the inner cannula 42 is withdrawn from the fluid path 26, the septum slit 25 closes the inner cannula from the fluid path and seals over the tip end 42a of the inner cannula as shown in FIG. 5.

Once the inner cannula 42 has been withdrawn to a point where the inner cannula tip 42a is about even with the outer cannula tip 37a, the septum slit 25 will no longer seal off over the tip of the inner cannula and the small amount of fluid trailing the tip of the inner cannula is now exposed to the vacuum source. It is at this point that the vacuum chamber 38 will begin to draw up the excess fluid that is in the septum slit 25 between an inner closed end thereof and the cannula tip 42a. There is an interstitial space between the inner cannula 42 and the outer cannula 37 leading into the vacuum chamber 38. As the inner cannula 42 is drawn up into the outer cannula 37, the sealing ring 44a draws away from the bottom of the vacuum chamber 38 to create a vacuum therein which draws residual fluid along said interstitial space and into the vacuum chamber 38. The one way valve 50, located between the vacuum chamber 38 and the syringe 52 prevents blood from being drawn out of the syringe and back into the vacuum chamber.

Figure 6:
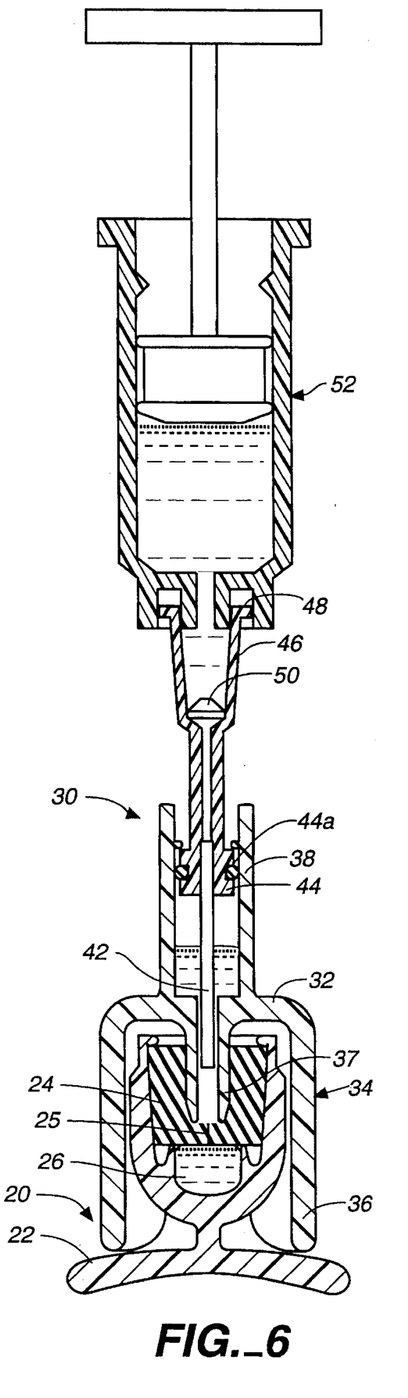
FIG. 6 is a view similar to FIG. 5 showing an inner cannula of the dripless cannula system of the present invention reaching its end of travel with respect to a vacuum chamber of the dripless cannula system, with a stop on the vacuum chamber to facilitate removal of the cannula from the sampling site.
Figure 7:
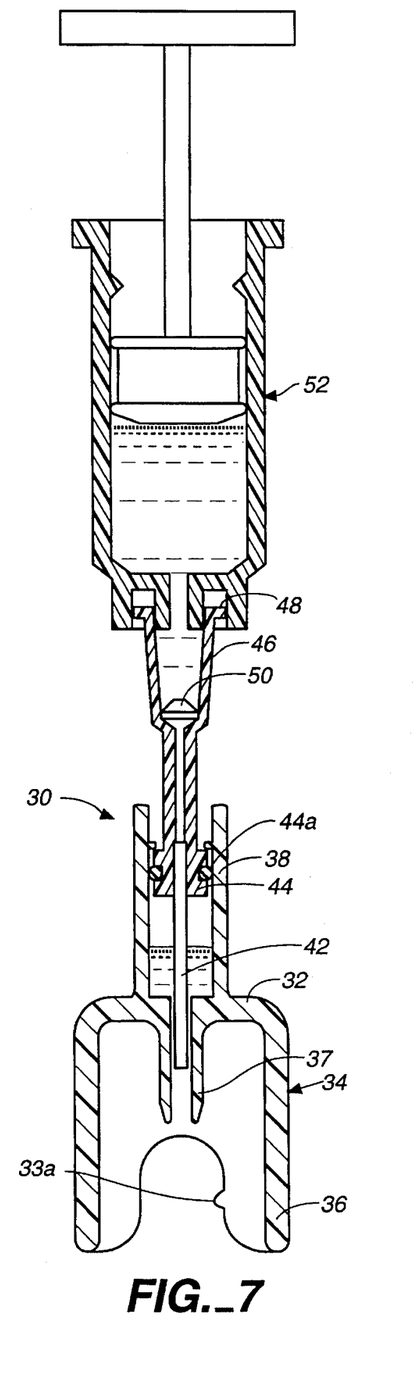
FIG. 7 is a view similar to FIG. 6, with the dripless cannula system of the present invention fully removed from the sampling site.

As the syringe 52 continues to draw the inner cannula 42 out of the slit 25 in the septum 24, excess fluid in the slit 25 of the septum 24 continues to flow into the vacuum chamber 38 which now functions as a reservoir for excess blood. The inner cannula 42 reaches the end of its travel (FIG. 6). Then the entire assembly pulls free of the sampling site 20 (FIG. 7). The system or assembly 30 is then removed from the syringe or blood collection tube 52 and discarded.

An alternative embodiment of the dripless cannula system is shown in FIGS. 8–12. The alternative system 101 has similar dimensions, is somewhat simpler than the preferred embodiment and includes a vacuum chamber 102 comprising a cylinder 104 having a distal end wall 106 and a proximal end 108 including a luer lock 109 connectable to the syringe 52. Cylindrical shield 110 extends downwardly from end wall 106. Disposed within the vacuum chamber 102 is a blunt cannula 112 carrying an annular retaining ring 114 at a distal end and an annular sealing member 116 carrying a sealing O-ring 116a fixedly mounted on a proximal end and disposed in the vacuum chamber 102.

Figure 8:
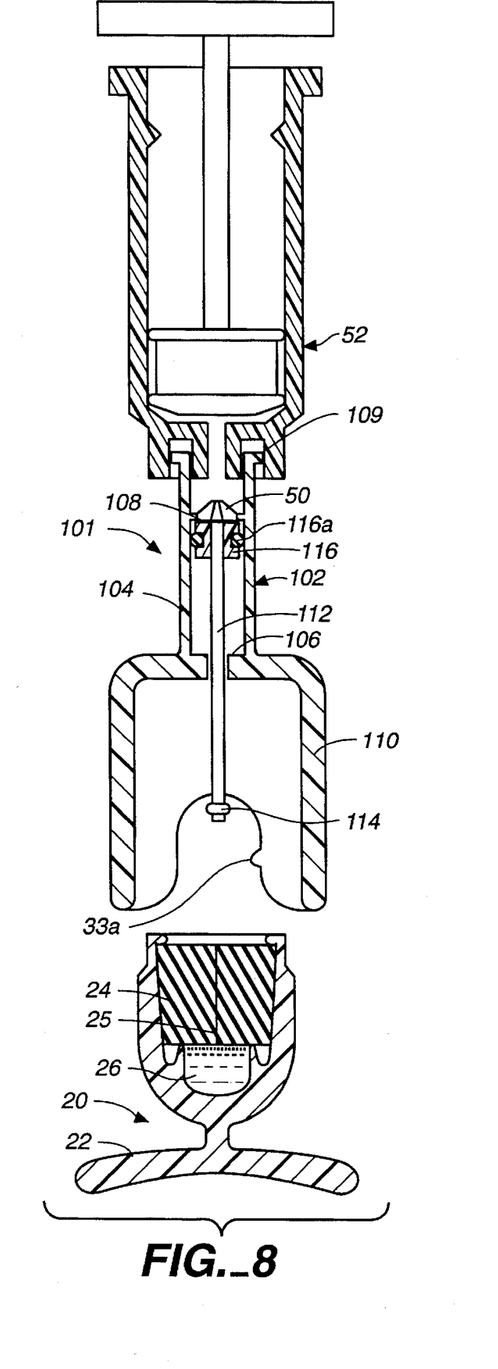
FIG. 8 is a sectional view similar to the view of FIG. 2, in which an alternative embodiment of the improved dripless cannula system of the present invention is shown disposed above a sampling site.
Figure 9:
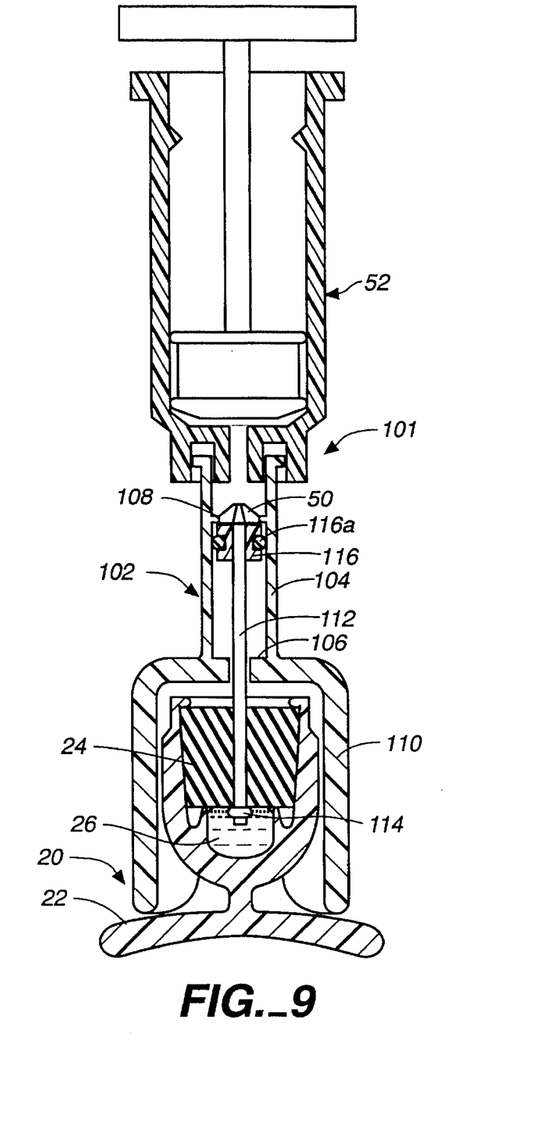
FIG. 9 is a view similar to FIG. 8, in which the alternative embodiment of the dripless cannula system of the present invention has been introduced into a sampling site to place a cannula of the system in the fluid flow path of the sampling site for a blood draw.
Figure 10:
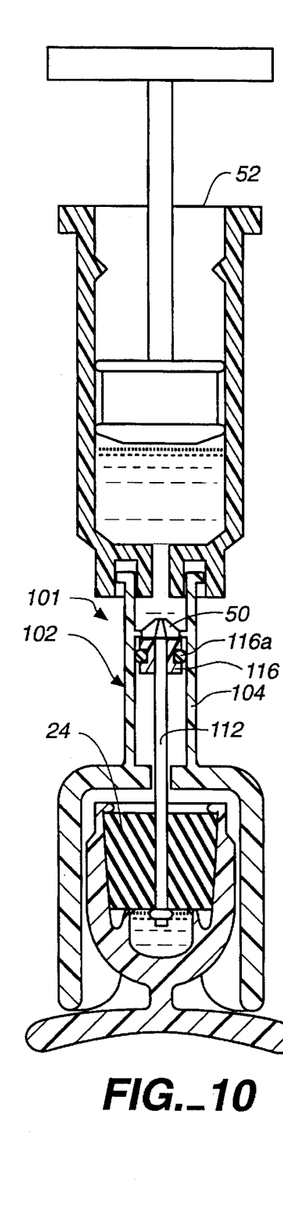
FIG. 10 is a view similar to view 9 in which a blood draw is in progress at the sampling site.
Figure 11:
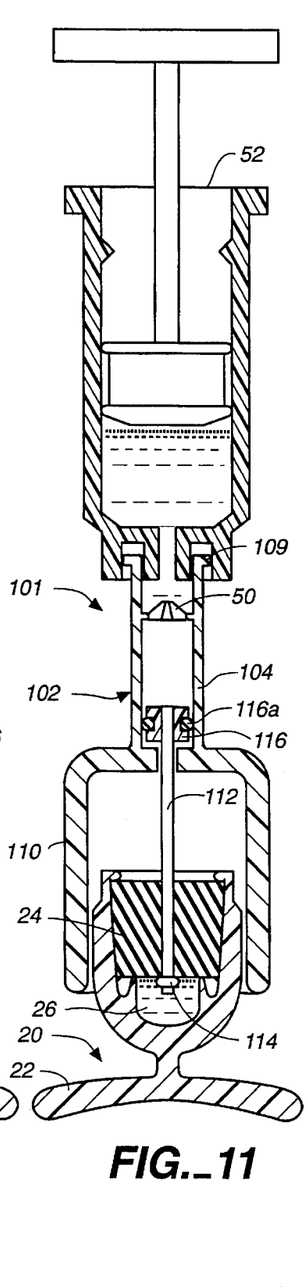
FIG. 11 is a view similar to FIG. 10 in which the blood draw is complete and the cannula of the alternative embodiment of the dripless cannula system of the present invention has not yet been withdrawn from the sampling site, but has reached an end of travel with respect to a vacuum chamber of the dripless cannula system, with a stop on the vacuum chamber to facilitate removal of the cannula from the sampling site.
Figure 12:
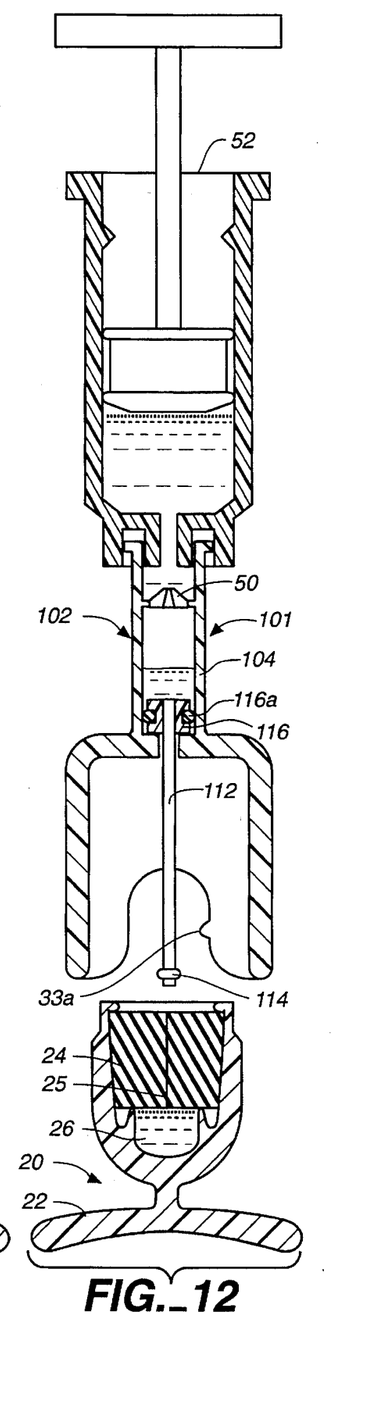
FIG. 12 is a view similar to FIG. 11, with the first alternative embodiment of the dripless cannula system of the present invention removed from the sampling site.

The alternative embodiment is operated as follows. Installation of the assembly on the syringe luer pushes the annular sealing member 116 to the upper end of the vacuum chamber 102 (FIG. 8). The inner cannula 112 is then fully inserted in the flow path 26 of sampling site 20 (FIG. 9). While the sampling process is in progress, blunt cannula 112 is disposed in fluid path 26 and sealing ring 116 remains at the upper end of vacuum chamber 102 (FIG. 10). Once the sampling process is complete and a full blood draw has been taken from the sampling site 20, cannula system 101 is pulled away from the sampling site 20 by the syringe 52. In FIG. 10 the annular retaining ring 114 disposed at the distal end of the cannula 112 engages septum 24 to draw the elastomeric seal 116 to the lower end of the vacuum chamber 102 and provides a vacuum in the vacuum chamber which draws residual fluid residing in the slit 25 in the septum up the cannula 112 and into the vacuum chamber (FIGS. 11 and 12). However, because of the frictional engagement of the cannula 112 with the bung, the alternative system 101 may not require a retaining ring 114 to draw the seal 116a to the bottom of vacuum chamber 102.

One disadvantage of the embodiment of FIG. 8–12 is that the stopcock 21a (FIG. 1) provided in the blood line 21 between the sampling site 20 and the catheter reposing in the patient must be closed. If stopcock 21a is not closed, the blood at the sampling site 20 is under arterial pressure and can be drawn into dripless cannula system 101.

A second alternative embodiment of the present invention shown in FIGS. 13-16, in which a dripless cannula system 201 comprises a blunt cannula 202 having an annular retaining ring 204 at a distal end thereof and a luer lock fitting 206 connectable to a syringe 52 at an upper end thereof. A shield 208 comprises a cylindrical body having a base 210, the base including a receptacle 211 and an open cylinder 212 extending down from the base. The shield 208 fits over the blunt cannula 202 through a central opening 214 in the base 210. Receptacle 211 receives a resistance plug 213, which includes a central bore which is then trapped within the receptacle 211 by a two-sided adhesive patch 218 at one side thereof. The resistance plug 213 is formed of a material which resists movement of the cannula therethrough such as silicone rubber. One side of the two-sided adhesive patch 218 is secured to the inner end of base 210 of the shield 208 and an opposite side of patch 218 receives a compressible plug 220 having a layer of absorbent material 221 thereon, and a central bore 222 receiving the cannula 202a.

Figure 13:
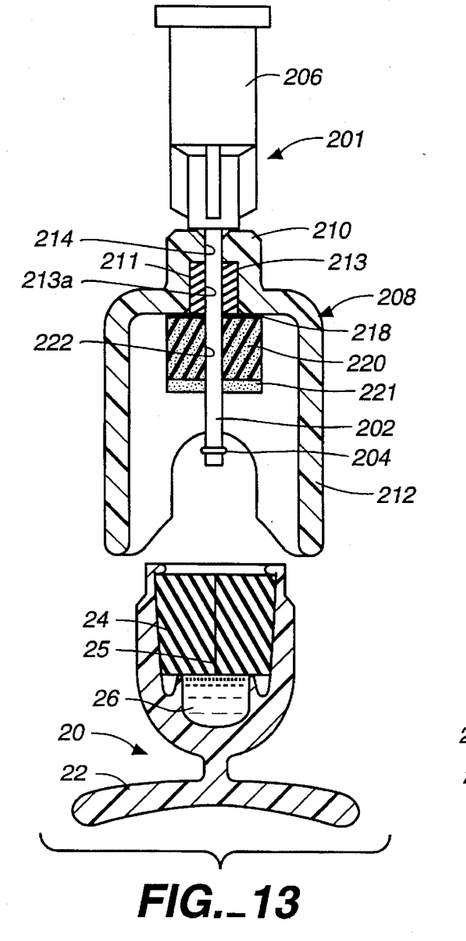
FIG. 13 is a view similar to FIG. 2 in which a second alternative embodiment of the dripless cannula system of the present invention is shown disposed above a sampling site.
Figure 14:
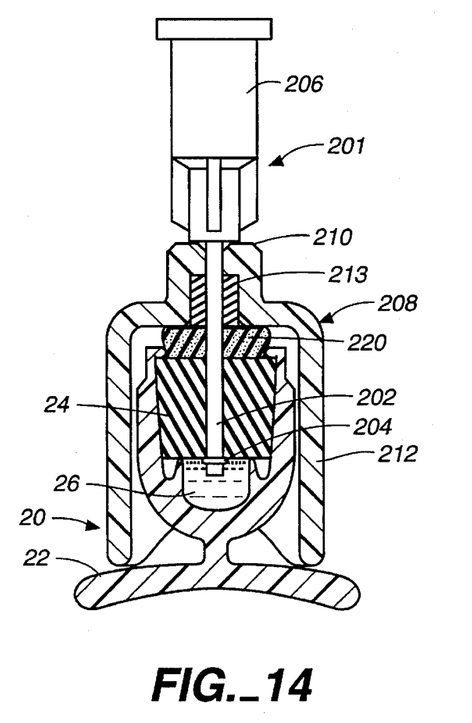
FIG. 14 is a view similar to FIG. 13 wherein the second alternative embodiment of the dripless cannula system of the present invention is inserted into the flow path of the sampling site for a blood draw.
Figure 15:
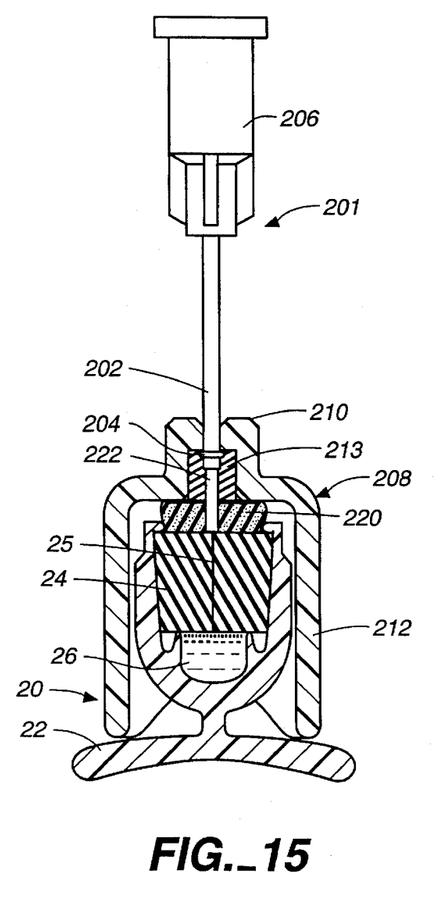
FIG. 15 is a view similar to FIG. 14 in which the blood draw is complete, and the cannula of the second alternative embodiment has been withdrawn from the fluid flow path of the sampling site.
Figure 16:
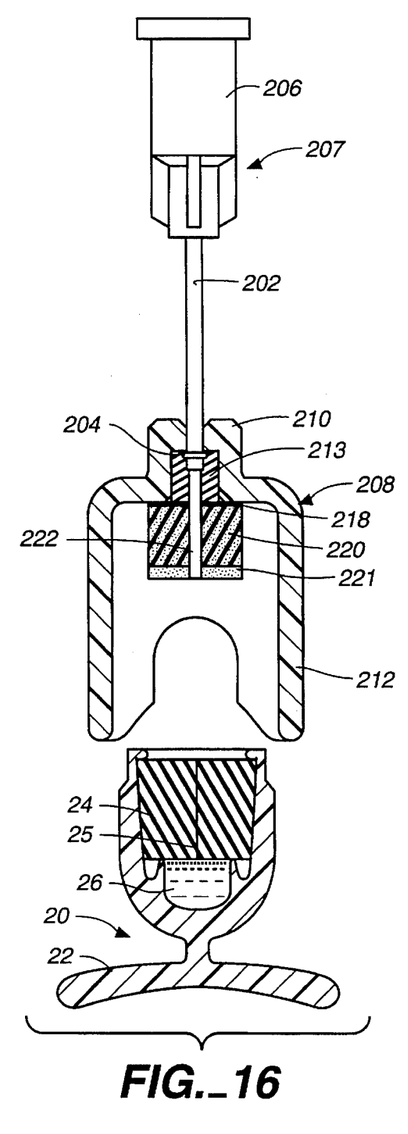
FIG. 16 is a view similar to FIG. 15 in which the second alternative embodiment of the dripless cannula system of the present invention has been removed from the sampling site.

FIG. 13 shows modified cannula system 201 above a sampling site 20. In FIG. 14, the tip of cannula 202 has been inserted through the bung 24 of the sampling site 20 and into fluid flow path 26. In FIG. 14, plug 220 is compressed. As the cannula 202 is withdrawn from the bung 24, resistance plug 213 slows withdrawal of the cannula 202 (FIG. 15 ) to enable the absorbent plug 220 to dwell at the sampling site 20 a longer time, thus to increase and enhance absorbency. As shown in FIG. 16, when cannula system 201 is fully withdrawn from sampling site 20, compressible plug 220 is returned to its original size and shape. Alternatively the embodiment of FIGS. 13–16 can be modified to remove receptacle 212 and resistance plug 213.

The present invention comprises a simple, effective, and efficient means of solving a serious problem in the hospital, that is the prevention of blood borne pathogens from reaching the care giver treating a critically ill patient. The invention is simple, comprising a minimum of parts, is effective because all of the parts are combined in an integrated and integral system and relatively inexpensive to provide. Moreover the present system solves a problem that has not been adequately addressed in the prior art known today.

While the description set forth describes a preferred embodiment of the present invention and two alternative embodiments thereof, it should be understood that within the parameters described other embodiments are possible. Accordingly, the present invention should not be limited to the embodiments set forth in the description above but rather should be considered with respect to the claims recited hereafter.

We claim:

1. A dripless cannula system usable with a fluid container for fluid sampling and operable to minimize fluid loss at a fluid sampling site, the system comprising:

a blunt cannula comprising an outer blunt cannula receiving an inner cannula therein for reciprocable movement, said blunt cannula having a distal end receivable in a fluid sampling site and a proximal end including structure capable of connecting said cannula to the fluid container and in locking fluid-tight engagement therewith, to provide a fluid path through said inner cannula from said sampling site to said fluid container; and fluid removing apparatus connected to the outer cannula and disposed about the inner cannula and in sealing relationship to prevent fluid flow between the sampling site and the fluid container, said apparatus operable following withdrawal of the inner cannula from the sampling site to receive residual fluids disposed at the sampling site by the sampling process.

2. A dripless cannula system as claimed in claim 1 wherein the fluid removing apparatus disposed about the cannula comprises a vacuum chamber having a base, a cylinder extending upwardly from the base and an upper end, said vacuum chamber including a reciprocable sealing member disposed on the inner cannula and apparatus enabling movement of the cannula through the vacuum chamber whereby fluid disposed between the inner cannula and the outer cannula is drawn into the vacuum chamber upon upward movement of the sealing member in the vacuum chamber.

3. The dripless cannula system as claimed in claim 2 wherein the sealing member associated with the cannula includes a lower structure carrying a sealing ring for the vacuum chamber, the sealing member having a bore therethrough, said bore receiving a proximal end of the cannula for fixed engagement therein at said lower structure to enable conjoint movement of the sealing member and the cannula in the vacuum chamber.

4. A dripless cannula system as claimed in claim wherein the enabling apparatus includes a one-way valve disposed between the fluid container and the vacuum chamber to prevent fluid in the container from being drawn into the vacuum chamber when the vacuum chamber is operative to withdraw residual fluid from the sampling site.

5. A dripless cannula system as claimed in claim 4 wherein an upper end of the enabling apparatus includes a luer locking member connectable to the fluid container usable in the sampling process.

6. A dripless cannula system as claimed in claim 5 wherein a shield member extends below the base of the vacuum chamber to shield the inner and outer cannula during the sampling procedure at the sampling site.

7. A dripless cannula system as claimed in claim 6 wherein the shield includes a detent engaging the sampling site to retain the dripless cannula system thereon.

8. A dripless cannula system as claimed in claim 1 wherein the fluid removing apparatus comprises a vacuum chamber having a base, a cylinder extending upwardly from the base and an upper end, said vacuum chamber including a reciprocable sealing member disposed on the inner cannula, said sealing member including a sealing ring fixedly mounted on the proximal end of the cannula for conjoint movement therewith and within the vacuum chamber and an annular retaining ring disposed at a distal end of the cannula for engagement with the sampling site to facilitate operation of the vacuum chamber when the dripless cannula is removed from the sampling site, whereby fluid disposed between the inner cannula and the outer cannula is drawn into the vacuum chamber upon upward movement of the sealing member in the vacuum chamber.

9. The dripless cannula system of claim 8 wherein a luer lock fitting is disposed above the vacuum chamber for engagement with a fluid container usable with the dripless cannula system to facilitate a fluid draw.

10. A dripless cannula system as claimed in claim 9 wherein a one-way valve is disposed above the vacuum chamber between the fluid container and the vacuum chamber to prevent fluid drawn into the fluid container from entering the vacuum chamber when the vacuum chamber is operable during the sampling process.

11. A dripless cannula system as claimed in claim 10 wherein a cylindrical shield is disposed below the vacuum chamber to extend at least the length of the cannula to minimize the possibility of unprotected fluid spray when the cannula is removed from the sampling site.

12. A dripless cannula system as claimed 11 wherein the shield includes a detent to retain the dripless cannula system at the sampling site while the sampling process is in progress.

13. A dripless cannula system as claimed in claim 1 wherein the distal end of the blunt cannula includes an annular retaining ring surrounding the cannula, the proximal end of the inner cannula is fixedly mounted in a luer fitting capable of being connected to a fluid container and the fluid-removing apparatus comprises a cylindrical shield overlying the cannula shield, the shield holding at its proximal end a plug of absorbent material having a bore therein for receiving the cannula, the bore enabling reciprocal movement of the cannula in the plug, the absorbent material retained at the sampling site when the cannula is withdrawn to absorb residual fluid generated by the sampling process.

14. The dripless cannula system of claim 13 wherein a resistance plug is disposed in the shield between the proximal end of the cannula and the plug of absorbent material, the resistance plug resisting withdrawal of the cannula from the sampling site so as to allow an increased dwell time of the absorbent material at the sampling site during withdrawal of the cannula to further facilitate absorption of residual fluid at the fluid sampling site.

15. A dripless cannula system usable with a fluid container for fluid sampling and operable to remove residual fluid from a fluid sampling site, said system comprising a blunt cannula comprising an outer blunt cannula receiving an inner cannula therein for reciprocable movement, said blunt cannula having a distal end receivable in a fluid sampling site and a proximal end including structure capable of connecting said cannula to the fluid container and in locking fluid-tight engagement therewith, to provide a fluid path through said inner cannula from said sampling site to said fluid container, a vacuum chamber connected to the outer cannula and disposed about the inner cannula in sealing relationship to prevent fluid flow between the sampling site and the fluid container, said vacuum chamber operable after the sampling process and during withdrawal of the inner cannula from the sampling site to remove residual fluids disposed at the sampling site by the sampling process.

16. A dripless cannula system as claimed in claim 15 wherein the vacuum chamber includes a base, a cylinder extending upwardly from the base, an upper end, and a reciprocable sealing member disposed on the inner cannula, said sealing member enabling movement of the inner cannula through the vacuum chamber, said sealing member carrying a sealing ring for the vacuum chamber, a bore provided in said sealing member for receiving a proximal end of the inner cannula for fixed engagement in said sealing member to enable conjoint movement of the sealing member and the cannula in the vacuum chamber, whereby fluid disposed between the inner cannula and the outer cannula is drawn into the vacuum chamber upon upward movement of the sealing member in the vacuum chamber.

17. A dripless cannula system as claimed in claim 1 wherein the enabling apparatus includes a one-way valve disposed between the fluid container and the vacuum chamber to prevent fluid in the fluid container from being drawn into the vacuum chamber when the vacuum chamber is operative to withdraw residual fluid from the sampling site.

18. A dripless cannula system as claimed in claim 17 wherein an upper end of the enabling apparatus includes a luer locking member connectable to a fluid container usable in the sampling process.

19. A dripless cannula system as claimed in claim 18 wherein a shield member extends below the base of the vacuum chamber to shield the inner and outer cannula during the sampling procedure at the sampling site.

20. A dripless cannula system as claimed in claim 19 wherein the shield includes a detent engaging the sampling site to retain the dripless cannula system thereon.

21. A dripless cannula system as claimed in claim 15 wherein the vacuum chamber includes a base, a cylinder extending upwardly from the base, an upper end, and a reciprocable sealing member disposed on the inner cannula, said sealing member including a sealing ring disposed in the vacuum chamber, said sealing ring fixedly mounted on the proximal end of the inner cannula for conjoint movement therewith and an annular retaining ring disposed at a distal end of the cannula for engagement with the sampling site to facilitate operation of the vacuum chamber when the inner cannula is removed from the sampling site.

22. The dripless cannula system of claim 21 wherein a luer lock fitting is disposed above the vacuum chamber for engagement with a fluid container usable with the dripless cannula system to facilitate a fluid draw.

23. A dripless cannula system as claimed in claim 22 wherein a one-way valve is disposed above the vacuum chamber between the fluid container and the vacuum chamber to prevent fluid drawn into the fluid container from entering the vacuum chamber when the vacuum chamber is operable during the sampling process.

24. A dripless cannula system as claimed in claim 23 wherein a cylindrical shield is disposed below the vacuum chamber to extend at least the length of the cannula to minimize the possibility of unprotected fluid spray when the cannula is removed from the sampling site.

25. A dripless cannula system as claimed in claim 24 wherein the shield includes a detent to facilitate retention of the dripless cannula system at the sampling site while the sampling process is in progress.

26. A dripless cannula system usable with a fluid container for fluid sampling and operable to minimize fluid loss at a fluid sampling site, said system comprising:

a blunt cannula having a distal end receivable in a fluid sampling site and a proximal end connectable to the fluid container in locking fluid-tight engagement therewith, to provide a fluid path therethrough from said sampling site to said fluid container;

a vacuum chamber disposed about the cannula and between the sampling site and the fluid container, the vacuum chamber having a base, a cylinder extending upward from the base, and an upper end;

an apparatus enabling movement of the cannula through the vacuum chamber, said apparatus carrying a sealing ring for the vacuum chamber, said apparatus including a central bore receiving a proximal end of the cannula for fixed engagement therewith, to enable conjoint movement of the sealing ring and the cannula in the vacuum chamber;

an outer blunt cannula provided in the base to receive an inner blunt cannula therein for reciprocable movement; and a one-way valve disposed in the enabling apparatus between the fluid container and the vacuum chamber to prevent fluid in the fluid container from being drawn into the vacuum chamber when the vacuum chamber is operative to withdraw residual fluid from the sampling site.

27. A dripless cannula system usable with a fluid container for fluid sampling and operable to minimize fluid loss at a fluid sampling site, said system comprising:

a blunt cannula having a distal end receivable in a fluid sampling site and a proximal end connectable to the fluid container in locking fluid-tight engagement therewith, to provide a fluid path therethrough from said sampling site to said fluid container;

a vacuum chamber disposed about the cannula and between the sampling site and the fluid container, the vacuum chamber having a base, a cylinder extending upward from the base, and an upper end;

a sealing ring disposed in the vacuum chamber, said sealing ring mounted on the proximal end of the cannula for conjoint movement therewith and an annular retaining ring disposed at a distal end of the cannula for engagement with the sampling site;

a luer lock fitting disposed above the vacuum chamber; and a one-way valve disposed between the fluid container and the vacuum chamber to prevent fluid drawn into the fluid container from entering the vacuum chamber when the vacuum chamber is operable during the sampling process.

28. A dripless cannula system usable with a fluid container for fluid sampling and operable to minimize fluid loss at a fluid sampling site, said system comprising a blunt cannula having a distal end receivable in a fluid sampling site and a proximal end connectable to the fluid container in locking fluid-tight engagement therewith, to provide a fluid path therethrough from said sampling site to said fluid container;

fluid removing apparatus disposed about the cannula and between the sampling site and the fluid container, said apparatus operable following withdrawal of the cannula from the sampling site to receive residual fluids disposed at the sampling site by the sampling process;

the distal end of the blunt cannula including an annular retaining ring surrounding the cannula, the proximal end of the cannula fixedly connectable to the fluid container; and a cylindrical shield overlying the cannula, the shield holding at its proximal end a plug of absorbent material having a bore therein for receiving the cannula, the bore in the absorbent plug enabling reciprocal movement of the cannula within the shield, the absorbent material temporarily retained at the sampling site when the cannula is withdrawn to absorb residual fluid generated at the sampling site by the sampling process.

29. The dripless cannula system as claimed in claim 28 wherein a resistance plug is disposed in the shield between the proximal end of the cannula and the plug of absorbent material, the resistance plug having a bore therein to receive the cannula, the bore of the resistance plug resisting withdrawal of the cannula from the sampling site so as to allow an increased dwell time of the absorbent material at the sampling site during withdrawal of the cannula to further facilitate absorption of residual fluid at the fluid sampling site.

30. A method of fluid sampling operable to minimize fluid loss at a fluid sampling site, said method comprising:

providing a blunt cannula having a distal end receivable in a fluid sampling site and a proximal end connectable to the fluid container in locking fluid-tight engagement therewith, to provide a fluid path therethrough from said sampling site to said fluid container;

disposing a vacuum chamber about the cannula and between the sampling site and the fluid container, the vacuum chamber having a base, a cylinder extending upward from the base, and an upper end;

providing an apparatus enabling movement of the cannula through the vacuum chamber, said apparatus carrying a sealing ring for the vacuum chamber, said apparatus including a central bore receiving a proximal end of the cannula for fixed engagement therewith, to enable conjoint movement of the sealing ring and the cannula in the vacuum chamber;

providing an outer blunt cannula in the base to receive an inner blunt cannula therein for reciprocable movement; and disposing a one-way valve in the enabling apparatus between the fluid container and the vacuum chamber to prevent fluid in the fluid container from being drawn into the vacuum chamber when the vacuum chamber is operative to withdraw residual fluid from the sampling site.

31. A method of fluid sampling operable to minimize fluid loss at a fluid sampling site, said method comprising:

providing a blunt cannula having a distal end receivable in a fluid sampling site and a proximal end connectable to the fluid container in locking fluid-tight engagement therewith, to provide a fluid path therethrough from said sampling site to said fluid container;

disposing a vacuum chamber about the cannula and between the sampling site and the fluid container, the vacuum chamber having a base, a cylinder extending upward from the base, and an upper end;

disposing a sealing ring in the vacuum chamber;

mounting said sealing ring on the proximal end of the cannula for conjoint movement therewith;

disposing an annular retaining ring at a distal end of the cannula for engagement with the sampling site;

disposing a luer lock fitting above the vacuum chamber; and disposing a one-way valve between the fluid container and the vacuum chamber to prevent fluid drawn into the fluid container from entering the vacuum chamber when the vacuum chamber is operable during the sampling process.

32. A method for fluid sampling operable to minimize fluid loss at a fluid sampling site, said method comprising:

providing a blunt cannula having a distal end receivable in a fluid sampling site and a proximal end connectable to a fluid container in locking fluid-tight engagement therewith, to provide a fluid path therethrough from said sampling site to said fluid container;

disposing fluid removing apparatus about the cannula and between the sampling site and the fluid container, said apparatus operable following withdrawal of the cannula from the sampling site to receive residual fluids disposed at the sampling site by the sampling process;

providing an annular retaining ring at the distal end of the blunt cannula, the proximal end of the cannula fixedly connectable to the fluid container;

providing a cylindrical shield overlying the cannula, the shield holding at its proximal end a plug of absorbent material having a bore therein for receiving the cannula;

enabling reciprocal movement of the cannula within the shield; and temporarily retaining the absorbent material at the sampling site when the cannula is withdrawn to absorb residual fluid generated at the sampling site by the sampling process.

* * * * *